(12) United States Patent
Schnaibel et al.

(10) Patent No.: US 8,075,759 B2
(45) Date of Patent: Dec. 13, 2011

(54) PROCEDURE FOR THE DETERMINATION OF THE LAMBDA VALUES WITH A BROADBAND LAMBDA PROBE

(75) Inventors: Eberhard Schnaibel, Hemmingen (DE); Erich Junginger, Stuttgart (DE); Johannes Kanters, Yokohama (JP); Thomas Moser, Schwieberdingen (DE); Frank Kowol, Ludwigsburg (DE); Reinhard Hein, Loechgau (DE)

(73) Assignee: Robert Bosch GmbH, Stuttgart (DE)

( * ) Notice: Subject to any disclaimer, the term of this patent is extended or adjusted under 35 U.S.C. 154(b) by 1070 days.

(21) Appl. No.: 11/472,144

(22) Filed: Jun. 21, 2006

(65) Prior Publication Data

US 2006/0289314 A1 Dec. 28, 2006

(30) Foreign Application Priority Data

Jun. 22, 2005 (DE) .......................... 10 2005 028 808
Oct. 20, 2005 (DE) .......................... 10 2005 050 269

(51) Int. Cl.
*G01N 27/409* (2006.01)

(52) U.S. Cl. .................. 205/784.5; 205/783.5; 205/784; 204/424; 73/23.31; 73/23.32

(58) Field of Classification Search .......... 204/424–429; 205/783.5–785; 73/23.31–23.32
See application file for complete search history.

(56) References Cited

U.S. PATENT DOCUMENTS

| | | | | |
|---|---|---|---|---|
| 5,034,112 A | * | 7/1991 | Murase et al. | ................ 204/406 |
| 5,249,453 A | * | 10/1993 | Usami et al. | ................ 73/23.32 |
| 5,265,458 A | * | 11/1993 | Usami et al. | ................ 73/23.32 |
| 2001/0052341 A1 | * | 12/2001 | Sasaki et al. | ............ 123/568.12 |

FOREIGN PATENT DOCUMENTS

| | | |
|---|---|---|
| DE | 102 16 724 C1 | 4/2002 |
| JP | 4-369471 | 12/1992 |
| JP | 6-273381 | 9/1994 |

* cited by examiner

*Primary Examiner* — Keith Hendricks
*Assistant Examiner* — Bach Dinh
(74) *Attorney, Agent, or Firm* — Merchant & Gould P.C.

(57) ABSTRACT

A procedure to calculate the Lambda value with a wideband Lambda sensor of an internal combustion engine of a motor vehicle is thereby characterized, in that from the measured pumping electricity and the sensitivities of the wideband Lambda sensor as well as the gas concentration ratios, in the lean operation an oxygen concentration and in the rich operation an oxygen deficit are determined and from these respectively a conclusion is drawn about the Lambda value using the Pischinger Formula.

3 Claims, 1 Drawing Sheet

PROCEDURE FOR THE DETERMINATION OF THE LAMBDA VALUES WITH A BROADBAND LAMBDA PROBE

FIELD OF THE INVENTION

The invention concerns a procedure for determining the characteristic curve of a Lambda sensor.

BACKGROUND OF THE INVENTION

A wideband Lambda sensor has been made known, for example, by the German patent DE 102 16 724 C1.

For such wideband Lambda sensors the lambda characteristic curve is ascertained by means of an explicit correlation of the needed functional pumping electricity to the lambda value. The correlation results thereby from measurements taken at the exhaust gas analysis station and in the vehicle itself. The lambda characteristic curve, which is measured at the exhaust gas analysis station, is presented in a technical documentation. In place of the characteristic curve measured at the exhaust gas analysis station and put down in the technical documentation, a characteristic curve applied to the internal combustion engine is deposited in an electronic control unit of the vehicle, for example as a data set. This characteristic curve is used for the regulation of the internal combustion engine. A lambda characteristic curve obtained in such a manner is not sufficient for a precise regulation.

A lambda sensor which has a diffusion element always shows in fact a diffusion displacement, which results from the fact that different types of gas with varying masses diffuse variably fast through a diffusion element. Depending upon the exhaust mixture, this diffusion displacement leads to a significant signal deviation from a nominal characteristic curve, as it was measured at the exhaust gas analysis station. The diffusion displacement causes thereby incorrect measurements in the vehicle, which can lead to big mistakes in the Lambda regulation of the internal combustion engine.

The task which has therefore necessitated the invention is to further develop a procedure for determining the characteristic curve of a wideband sensor to the point where the diffusion displacements of the gas components, which were discussed previously, or the total lack of one or several of the gas components can be taken into account when determining the lambda value. The invention also particularly encompasses the determination of Lambda in internal combustion engines that are driven by hydrogen, ethanol or CNG (compressed natural gas).

SUMMARY OF THE INVENTION

The invention fulfills this task mentioned above with the characteristics of claim 1.

It is the fundamental idea of the invention to no longer assign a rigid pumping electricity to the Lambda sensor at a measured Lambda; but basically to measure the sensitivity of the sensor against specific gas components. The pumping electricity can be allocated to the gas mixture by way of the sensitivity, in that the resulting total (cumulative) pumping electricity for a gas mixture is calculated from the superimposition, that is from the sum of the individual sensitivities of the respective gas types existing on the wideband sensor multiplied by their concentration.

At a lambda value less than 1 an alternative pumping electricity is determined in the above manner, with which an oxygen deficit to a certain extent can be counted on. For a Lambda value greater than 1, the oxygen measured in the exhaust is cited. In this manner a characteristic curve can be indicated across the entire Lambda range by means of the inherently familiar, so-called Pischinger Formula.

Due to this procedure the Lambda control characteristic curve in the automobile can be to a great extent more precisely determined; and thus a far better regulation prior to the catalytic converter can be undertaken. In so doing, the toxic emissions decrease.

Furthermore, the regulation is far more stabile. This leads to a longer life for the catalytic converter, and, consequently, results in a saving of the raw materials used for the construction of the catalytic converters. It proves to be particularly advantageous for the detection of errors, in that the individual sensor properties (characteristics) can be distinguished from the influences of the exhaust on the characteristic curve of the wideband Lambda sensor.

BRIEF DESCRIPTION OF THE DRAWINGS

Further advantages and characteristics of the invention are the subject matter of the following description of the embodiment examples of the invention in connection with the drawing. In the drawing.

DETAILED DESCRIPTION OF THE PREFERRED EMBODIMENT

Figure 1:
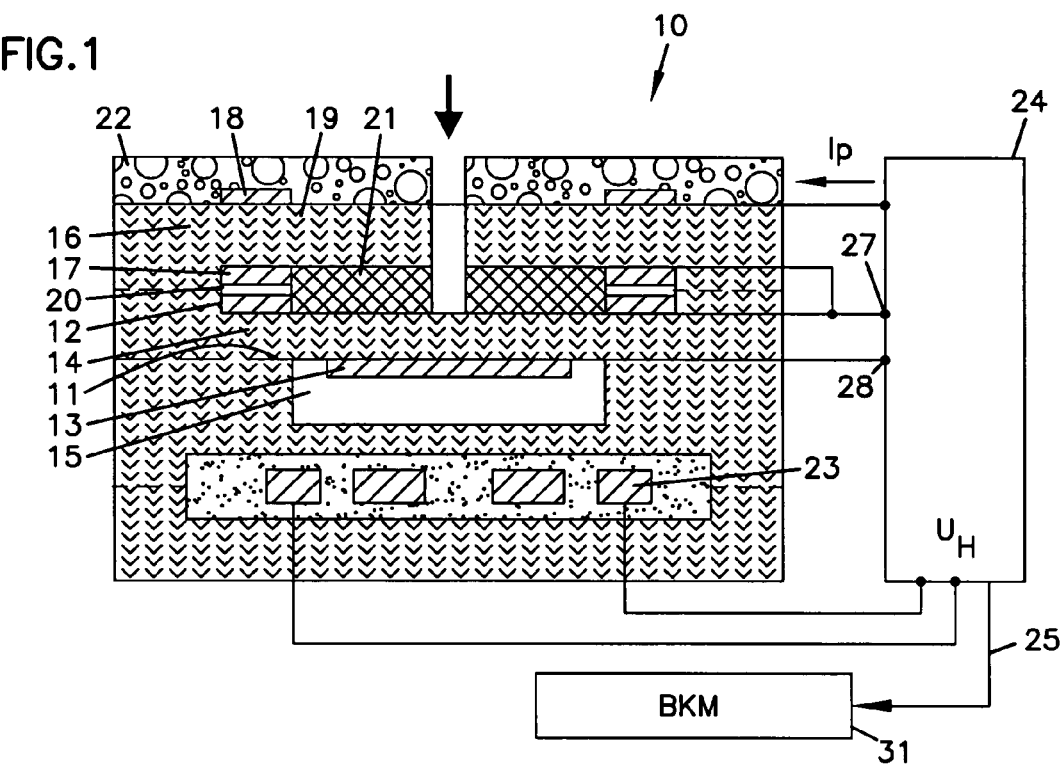
FIG. 1 shows schematically a cross-section of a wideband Lambda sensor and a block diagram concerning its activation.

The wideband lambda sensor 10, which is schematically diagramed in cross-section, serves to determine the gas components, particularly the oxygen concentration in exhausts from internal combustion engines, in order to receive a control signal for the adjustment of a fuel-air-mixture with which the internal combustion engine is driven. The Lambda sensor possesses a measurement or Nernst cell 11 with a measurement electrode 12 and a reference electrode 13, that are both arranged on a solid electrolyte 14, as well as a pumping cell 16 with an outside electrode 18—also known as outer pumping electrode or OPE for short—and with an inside electrode 17—also known as inner pumping electrode or IPN for short as it lies with the Nernst electrode on the same potential. These (outside and inside electrodes) are likewise arranged on a solid electrolyte. A zirconium oxide stabilized with yttrium oxide is used as the stable electrolyte. The reference electrode 13 is arranged in a reference canal, which is acted upon by a reference gas, usually air. The inside electrode 17 of the pumping cell 16 is together with a measurement cell 12 of the Nernst cell 11—also called Nernst electrode—arranged in a measurement compartment 20, which stands by way of a diffusion barrier 21 in connection with the exhaust of the internal combustion engine. The outside electrode 18 is covered by a porous protective layer 22 and is exposed directly to the exhaust. A heating device 23, which is formed from a so-called heating meander, additionally belongs to the Lambda sensor. The heating device 23 is being acted upon by a heating voltage $U_H$ and is kept at a constant operational temperature of, for example, 780° C. The Lambda sensor 10 is operationally connected to an electronic control device 20, that generates for its part control signals for adjusting the fuel-air-mixture in the internal combustion engine. The internal combustion engine is depicted as a block in the figure, whose activation by the control device 24 is symbolized by the signal lead 25. The pumping cell 16 is connected to the control device 24 by way of terminals 26 and 27, whereby the outside electrode 18 is linked up at terminal 26 and the inside electrode 17 at terminal 27. The Nernst cell 11 is connected by way of terminals 27 and 28 with the control device 24. In so doing, the measuring electrode 12 is linked up at the terminal 27 and the reference electrode 13 at the terminal 28. Between the terminals 27 and 28 the detection or Nernst voltage $U_N$ is able to be tapped and the pumping voltage $U_P$ is available at the terminals 26, 27. The electronic control device 24 has an unspecified regulating switch, with which the pumping voltage $U_P$ is adjusted against the Nernst voltage $U_N$. The latter is in turn dependent upon the proportion of oxygen, to which the measurement electrode 12 and the reference electrode 13 are exposed.

The Lambda sensor is operated in the following manner with the previously described electronic control device 24. Due to the difference in oxygen concentration present between the measuring electrode 12 and the reference electrode 13, a certain Nernst voltage $U_N$ turns up, which is a measurement for the oxygen concentration in the measuring compartment 20. A pumping voltage $U_P$ lying at pumping cell 16, which drives a pumping current $I_P$ across the pumping cell 16, is adjusted against a Nernst voltage $U_N$. Depending upon the composition of the exhaust and with that the oxygen content of the exhaust, this pumping current $I_P$ is cathodic—as depicted in the figure—or anodic. In the first instance, the outside electrode 18 is operated as an anode and the inside electrode 17 as a cathode; and in the second instance, the opposite occurs. The outside electrode 18 is operated as a cathode and the inside electrode 17 as an anode. The pumping current $I_P$ is cathodic at a stable operation of the internal combustion engine with a fuel-air-mixture in a lean operation. That is to say the inside electrode 17 of the pumping cell 16 is cathodically loaded. At a stabile operation of the internal combustion engine 31 with the air-fuel-mixture in the rich range, the pumping current $I_P$ is anodic. That is to say the inside electrode 17 of the pumping cell 16 is anodically loaded. In the former case oxygen ions are pumped out of the measuring compartment 20; and in the latter case the oxygen ions are pumped from the exhaust into the measuring compartment 20. The pumping voltage $U_P$ is thereby so regulated, that a constant oxygen concentration appears in the measuring compartment 20, which brings about a constant Nernst voltage of, for example, 450 m V. The pumping current $I_P$ which appears is a measurement for the oxygen concentration, respectively the oxygen deficit in the exhaust and is recorded as measuring voltage. The correspondingly appropriate Lambda value is then determined from a characteristic curve.

Figure 2:
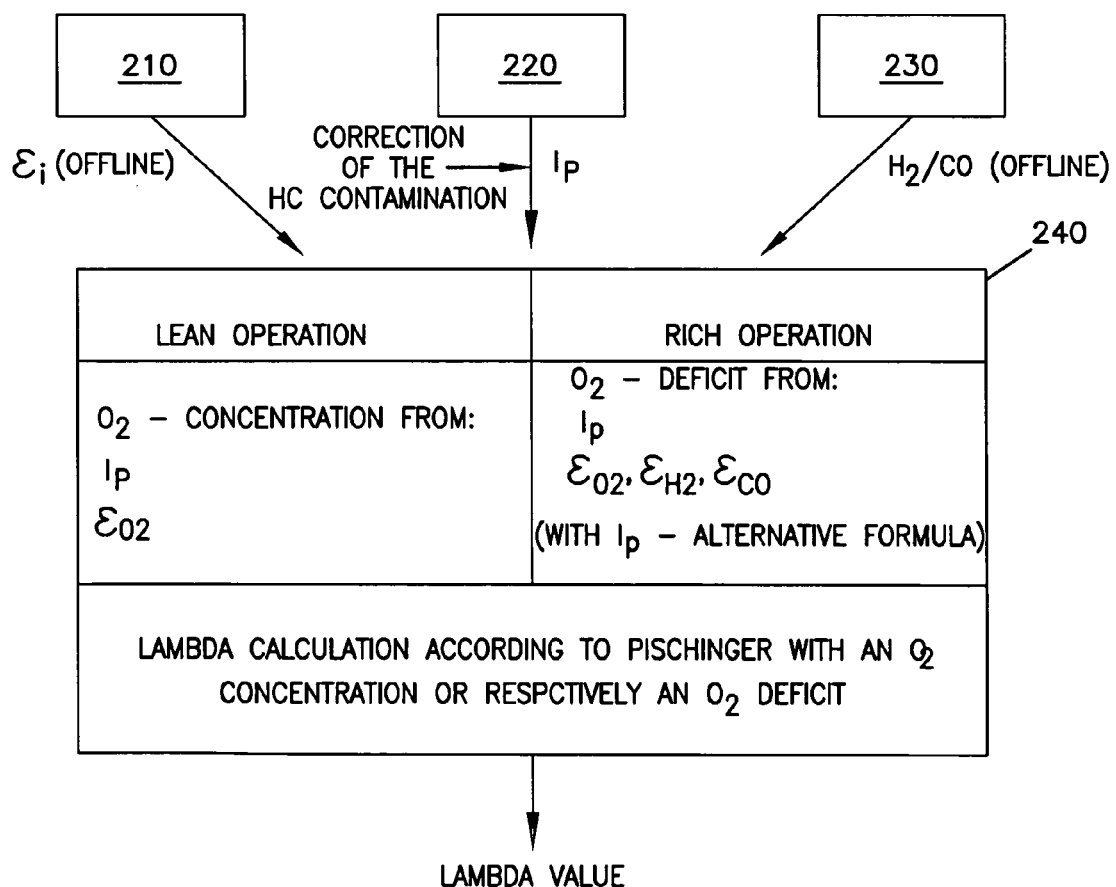
FIG. 2 shows schematically a block diagram for the explanation of the procedure according to the invention.

To determine a Lambda characteristic curve, the gas sensitivities of the wideband Lambda sensor or a two point Lambda sensor are first specified off-line at a gas analysis station, in that the sensor 10 is exposed to the respective gas or gas mixture to be measured, and the resulting pumping current $I_P$ is measured (FIG. 2, Step 210). In this manner sensitivity values of all the relevant exhaust components in the exhaust of the internal combustion engine are determined and put down in a technical documentation. This specification of the gas sensitivities in Step 210 occurs previously in the laboratory. The measurement of the gas concentration proportions in the internal combustion engine likewise is carried out previously off-line (Step 230). During the operation of the internal combustion engine, the pumping current $I_P$ is registered by the previously described wideband Lambda sensor and forwarded in Step 220 to the electronic control device 24. The calculation of the Lambda value (Step 240) occurs in the control device 24, whereby it is distinguished between a lean operation, in which an oxygen concentration is calculated from the oxygen sensitivity $\epsilon_{O2}$ which was previously determined offline, and a rich operation, in which an oxygen deficit is calculated as a result of the measured pumping current $I_P$ and the gas sensitivities of oxygen, hydrogen and CO (carbon monoxide): $\epsilon_{O2}$, $\epsilon_{H2}$, $\epsilon_{CO}$, as well as the previously determined gas ratio K. That is to say from the ratio of hydrogen to carbon monoxide. This gas concentration ratio K hardly changes during the operation of the internal combustion engine. This calculation directive may also be applied to internal combustion engines, in which one or more of the gas components are not present, for example, in hydrogen motors.

From the thusly determined oxygen concentration in the lean operation, respectively the oxygen deficit in the rich operation, the Lambda value is calculated as is described more closely in the following manner by means of the so-called Pischinger Formula, an empirical formula for the calculation of the Lambda values.

The determination of the Lambda value in a rich operation is explained in more detail as follows: In a rich operation the measured pumping current $I_P$ is converted into an alternative pumping current $I_{P\text{-}Alternative}$, which corresponds to the theoretical pumping current $I_P$ of the oxygen deficit. To calculate the alternative pumping current $I_{P\text{-}Alternative}$ from the measured pumping current $I_P$, two equations are drawn upon. The first of these two equations shows the calculation of the pumping current $I_P$ from the measured exhaust concentrations for $H_2$ and CO $x\_H_2$ and $x\_CO$ and the sensitivities $\epsilon\_H_2$ and $\epsilon\_CO$ of the wideband Lambda sensor for these gases.

$$I_{p\text{-}measured} = x\_H_2 \cdot \epsilon\_H2 + x\_CO \cdot \epsilon\_CO \tag{I}$$

It is to hereby be noted, that the exhaust concentrations are those values of the so-called moist exhaust. The measurement values obtained with the help of a gas analysis for the gases: carbon monoxide CO, hydrogen $H_2$ and oxygen $O_2$ in the dried exhaust are converted into values for the moist exhaust. In so doing only the values for carbon monoxide and hydrogen $H_2$ are taken into account. The oxygen deficit is determined using the following equation:

$$I_{p\text{-}alternative} = (x\_H_2 + x\_CO) \cdot 0.5 \cdot (-\epsilon\_O_2) \tag{II}$$

Dividing these two equations results in the following value for the alternative pumping current, when the ratio of hydrogen to carbon monoxide is taken into consideration: $K = x\_H_2 / x\_CO$:

$$I_{p\text{-}Alternative} = \frac{-I_{Pmeasured}}{2} \frac{(K+1) \cdot (-\varepsilon\_O_2)}{K \cdot \varepsilon\_H_2 + \varepsilon\_CO} \tag{III}$$

Hence, the alternative pumping current is determined from the gas concentration ratio of hydrogen to carbon monoxide, which was previously measured offline, as well as from the sensitivities of the sensor to oxygen, hydrogen and carbon monoxide. This calculation directive is then also still valid, in the case that no hydrogen or carbon monoxide are present in the exhaust. That is to say if K=0 (no hydrogen present) or K→∞ (no carbon monoxide present). The formula simplifies itself then as follows:

$$K \to 0: I_{p\text{-}Alternative} = \frac{-I_{Pmeasured}}{2} \frac{\varepsilon\_O_2}{\varepsilon\_CO} \tag{IV}$$

$$K \to \infty: I_{p\text{-}Alternative} = \frac{-I_{Pmeasured}}{2} \frac{\varepsilon\_O_2}{\varepsilon\_H_2} \tag{V}$$

In a rich operation, that is when $I_P \leq 0A$ the oxygen deficit $x\_O_2$ is determined from the alternative pumping current (as determined in the above equations) and from the known sensitivity to oxygen $\epsilon\_O_2$.

$$x\_O_2 = I_{p\text{-}Alternative}/\epsilon\_O_2.$$

In the lean operation, that is when the pumping current is greater than OA, the oxygen concentration is determined directly from the measured value of the pumping current $I_{P\text{-}Measured}$ and from the sensitivity of the sensor to oxygen.

$$x\_O_2 = I_{p\text{-}measured}/\epsilon\_O_2.$$

From the oxygen value $x\_O_2$, that is to say in the case of the rich operation from the oxygen deficit or in the case of the lean operation from the oxygen concentration, the Lambda value is determined with the help of an empirical formula for the calculation of the Lambda value according to Pischinger:

$$\lambda = (1 + (((n/m \cdot 4)/(1 + n/m \cdot 4)) \cdot X_{O2}))/(1 - (4.764 \cdot X_{O2})),$$

With m, n $\epsilon$ {0, 1, 2, . . . } from $C_mH_nO_k$ of the fuel, $X_{O2}=O_2$–Concentration/Deficit.

The big advantage of this determination of the Lambda value by means of a wideband sensor is apparent therein, that only one measurement, namely the measurement of the pumping current $I_P$ is required, in order to be able to exactly determine the Lambda value in the rich operation as well.

The application of the previously described procedure in an internal combustion engine additionally makes possible for HC-corrections in the lean operation, resulting in an increase in exactness. In the lean operation with an increasing Lambda, a growing mistake dispersion and an increasing deviation from the Lambda value, $\lambda\_obtained$ from the so-called Brettschneider Formula are observed. The reason for this is assumed to lie with greater variations of the HC-concentrations. Under the assumption that the approximate proportion of HC in the lean operation can be put down in a characteristic curve, the alternative pumping current $I_{P\text{-}alternative}$ can be calculated by means of an assumed post-combustion, when the ideal combustion equation is taken into consideration.

$$C_mH_n + (m + n/4) \cdot O_2 \rightarrow m \cdot CO_2 + n/2 \cdot H_2O.$$

Thereby different hydrocarbons react in the following proportions with oxygen:

| | |
|---|---|
| 1 Vol. % $C_2H_4$ | 3 Vol. % $O_2$ |
| 1 Vol. % $C_3H_6$ | 4.5 Vol. % $O_2$ |
| 1 Vol. % $C_3H_8$ | 5 Vol. % $O_2$ |

The following steps comprise the procedure for HC-correction.

1. For the exhaust concentration of the moist exhaust, the pumping current $I_P$ is calculated from the exhaust concentrations of $O_2$ and HC. The other exhaust components are in contrast neglected.

$$I_{p\text{-}measured} = I_P O_2 + I_P H_c$$

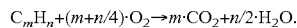

2. The proportion of the measured $I_P$, which is determined by way of $O_2$, is:

$$I_P O_2 = x\_O_2 \cdot \epsilon\_O_2 = (I_{p\text{-}measured} - x\_HC \cdot \epsilon\_HC)$$

Hence, the following results for the $O_2$–concentration for $I_P O_2$:

$$x\_O_2 = (I_{p\text{-}measured} - x\_HC \cdot \epsilon\_HC)/\epsilon\_O_2$$

3. The $O_2$–surplus is calculated for the application of the Pischinger Formula. In so doing, it is assumed that the available HC reacts completely with the $O_2$: $x\_O_{2\text{-}surplus} = x\_O_2 - (x\_HC\_ppm\_C^{1/3}) \cdot 4.5$ for $C_3H_6$ whereby it must be taken into consideration, that due to the $C_3H_6$ $_{molecule}$, only $1/3$ of the carbon withdrawal is taken into consideration in the formula.

The Lambda value is calculated from this oxygen surplus $x\_O_{2\ surplus}$ using the previously described Pischinger Formula. By way of the previously described HC-correction, the more middle deviation of the value $\lambda_{Brettschneider}$ can be significantly reduced. This results in the Lambda value allowing itself to be much more accurately determined.

The invention claimed is:

1. A method of determining a Lambda value of internal combustion engine exhaust gas with a wideband Lambda sensor, the method comprising:
   measuring a pumping current, wherein the pumping current is a function of oxygen concentration in the exhaust gas;
   calculating a first oxygen concentration when the pumping current is cathodic, corresponding to an air-fuel mixture in a lean condition, the first oxygen concentration calculated from the measured pumping current and an oxygen sensitivity parameter;
   otherwise, calculating a second oxygen concentration when the pumping current is anodic, corresponding to the air-fuel mixture in a rich condition, the second oxygen concentration calculated from a hydrogen sensitivity parameter, a carbon monoxide sensitivity parameter, a gas concentration ratio, the measured pumping current, and the oxygen sensitivity parameter utilizing an equation $$I_{p\text{-}Alternative} = \frac{-I_{pMeasured}}{2} \frac{(K+1) \cdot \varepsilon\_O_2}{K \cdot \varepsilon\_H_2 \cdot \varepsilon\_O_2},$$

wherein $I_{pMeasured}$ is the measured pumping current, K is the gas concentration ratio, $\epsilon\_O_2$ is the oxygen sensitivity parameter, and $\epsilon\_H_2$ is the hydrogen sensitivity parameter; and
   determining the Lambda value from one of the first oxygen concentration and the second oxygen concentration;
   wherein the gas concentration ratio is a predetermined measurement of gas concentration proportions in the internal combustion engine comprising a ratio of hydrogen concentration to carbon monoxide concentration.

2. The method according to claim 1, wherein the oxygen sensitivity parameter, the hydrogen sensitivity parameter, and the carbon monoxide sensitivity parameter are predetermined parameters of the Lambda sensor.

3. The method according to claim 1, further comprising recording gas concentrations in the exhaust gas of the internal combustion engine against a number of revolutions-load-range.

* * * * *